United States Patent [19]

Shroff et al.

[11] 4,283,541

[45] Aug. 11, 1981

[54] PYRIDYLACYL-HYDROXAMATES

[75] Inventors: James R. Shroff, Riverside, Conn.; Rohit Desai, Yonkers, N.Y.

[73] Assignee: USV Pharmaceutical Corporation, Tuckahoe, N.Y.

[21] Appl. No.: 153,480

[22] Filed: May 27, 1980

[51] Int. Cl.³ .................................................. C07D 213/56
[52] U.S. Cl. ...................................... 546/336; 546/337
[58] Field of Search .................................. 546/336, 337

[56] References Cited

U.S. PATENT DOCUMENTS 2,146,392  2/1939  Baldwin et al. .................. 546/336

Primary Examiner—John M. Ford
Attorney, Agent, or Firm—Ernest B. Lipscomb, III

[57] ABSTRACT

Compounds of the formula

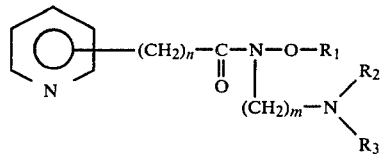

wherein
$R_1$, $R_2$ and $R_3$ are independently hydrogen, lower alkyl, phenyl or phenyl-lower alkyl,
n is an integer from 1 to 5, and
m is an integer from 2 to 5 have antiarrhythmic activity.

8 Claims, No Drawings

PYRIDYLACYL-HYDROXAMATES

This invention relates to new organic compounds possessing valuable pharmacological activity. In particular, the invention relates to pyridylalkanoylhydroxamates of the structure

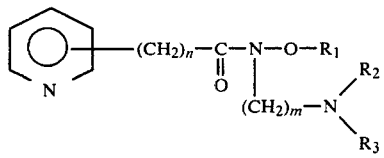

wherein
$R_1$, $R_2$ and $R_3$ are independently hydrogen, lower alkyl, phenyl, or phenyl-lower alkyl,
n is an integer from 1 to 5, and
m is an integer from 2 to 5.

The lower alkyl groups in $R_1$, $R_2$ and $R_3$ contain from 1 to 6 carbon atoms and may be straight chain or branched. These groups include methyl, ethyl, propyl, isopropyl, butyl, sec-butyl, amyl, isoamyl, hexyl and the like. These alkyl groups may carry substituents such as halogen, hydroxy, lower alkoxy, amino, mono- and di-(lower alkyl)amino, carboxy, and carbo-lower alkoxy.

The phenyl group in phenyl per se and in phenyl-lower alkyl may carry substituents such as halogen, hydroxy, lower alkoxy, amino, mono- and di-(lower alkyl)amino, lower alkyl, carboxy, carbo-lower alkoxy, carbamido, and trihaloalkyl such as trifluoromethyl.

Preferably, the pyridyl is substituted in the 2-position, n is 1, m is 2, and $R_1$, $R_2$ and $R_3$ are lower alkyl.

The compounds of the present invention may be prepared by the following sequence of reactions:

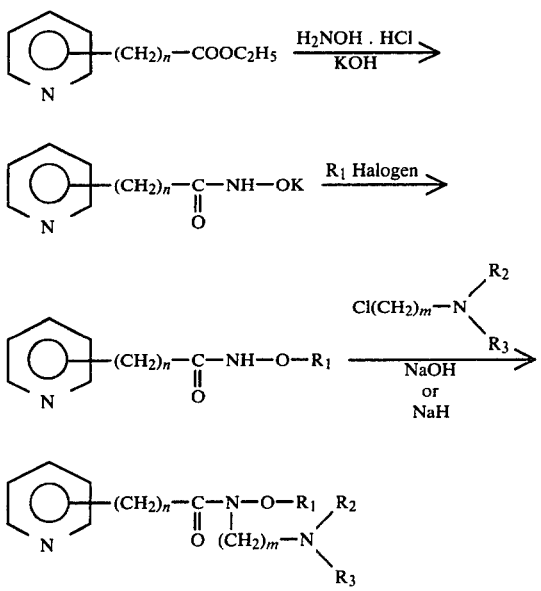

The invention will be more fully illustrated in the examples that follow. These examples are given by way of illustration and are not to be considered as limiting.

EXAMPLE I

Potassium-2-pyridylacetohydroxamate

Hydroxylamine hydrochloride (85.3 gm, 1.2 mol) was dissolved in 280 ml methanol at the boiling point (65° C.). At the same time potassium hydroxide (101.3 gm, 1.8 mol) was dissolved in 280 ml methanol at the boiling point (65° C.). Both solutions were cooled slowly to below 40° C. When crystallization of hydroxylamine hydrochloride began, the potassium hydroxide solution was added to it with vigorous stirring. The reaction mixture was cooled in an ice bath for 5–10 minutes to facilitate precipitation of potassium chloride. Ethyl pyridylacetate (96.4 gm, 0.57 mol) was added to the stirred reaction mixture and the reaction mixture immediately filtered. The solvent was removed from the filtrate and the oily residue crystallized from isopropanol to give 74.1 gm (68% yield) of potassium-2-pyridylacetohydroxamate, m.p. 128°–129° C.

EXAMPLE II

O-Ethyl-2-pyridylacetohydroxamate

A mixture of potassium 2-pyridylacetohydroxamate (19.0 gm, 0.1 mol) and ethyl bromide (10.5 gm, 0.1 mol) was dissolved in 120 ml methanol and the reaction mixture refluxed for a period of about 12 hours. The postassium bromide was filtered off, and the solvent removed from the filtrate. The oily residue was triturated with acetonitrile, filtered, washed with a saturated sodium chloride solution, and extracted with chloroform (3×50 ml). The combined chloroform extracts were dried (MgSO$_4$), filtered, and evaporated to yield 8.0 gms of a yellow oil, (44.4% yield).

EXAMPLE III

O-Ethyl-N-(N,N-diisopropylaminoethyl)-2-pyridylacetohydroxamate

To a slurry of sodium hydride (2.6 gms, 0.55 mol, 50:50 oil dispersion) in a dry dimethylformamide under $N_2$ atmosphere was added a solution of O-ethyl-2-pyridylacetohydroxamate (9.0 gm, 0.05 mol) in dimethylformamide (50ml). A gas bubbler was attached, the nitrogen flow discontinued and the mixture was warmed in a bath until bubbling ceased. From the dropping funnel a solution of N-(2-chloroethyl)-diisopropylamine (8.2 gm, 0.05 mol) in toluene (100 ml) was added slowly. The reaction mixture was heated at 90°–100° C. for two hours, allowed to cool and vacuum filtered. The filtrate was evaporated in vacuo to a dark oil. The oily material was extracted with chloroform (2×50 ml), washed with 1 N sodium hydroxide, dried (MgSO$_4$), filtered and evaporated to yield 16.0 gms of crude product. Distillation of the crude product gave 4.0 gms (26.6%) of material as a yellow liquid, bp 126°–128° C. (0.2 mm).

Following the procedures described above, the following additional compounds were prepared:

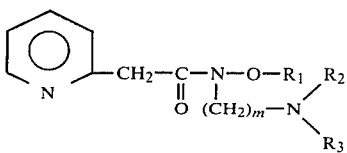

| $R_1$ | $R_2$ | $R_3$ | m |
|---|---|---|---|
| $C_2H_5$ | $i\text{-}C_3H_7$ | $i\text{-}C_3H_7$ | 3 |
| $C_6H_5CH_2$ | $i\text{-}C_3H_7$ | $i\text{-}C_3H_7$ | 2 |

In in vivo screening against chloroform induced ventricular arrhythmia in mice, the compounds exhibited an $ED_{50}$ of about 10 to 30 mg/kg. This will enable a physician to select the proper dose for the patient depending upon age, weight, sex and other considerations. The compound wherein n is 1, m is 2, $R_1$ is ethyl and $R_2$ and $R_3$ are isopropyl is the most active.

The compounds may be mixed with solid or liquid pharmaceutical carriers and formulated into tablets, powders or capsules for oral administration or dissolved in suitable solvents for either oral or parenteral administration.

We claim:

1. A compound of the formula

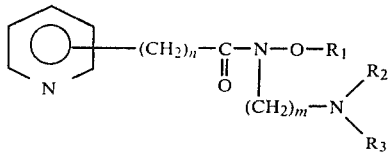

wherein
$R_1$, $R_2$ and $R_3$ are independently hydrogen, lower alkyl, phenyl or phenyl-lower alkyl,
n is an integer from 1 to 5, and
m is an integer from 2 to 5.

2. A compound of the formula

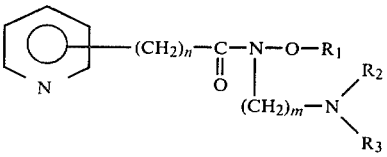

wherein
$R_1$, $R_2$ and $R_3$ are independently lower alkyl, phenyl or phenyl-lower alkyl,
n is an integer from 1 to 5, and
m is an integer from 2 to 5.

3. A compound according to claim 2 wherein n is 1.
4. A compound according to claim 3 wherein m is 2 or 3.
5. A compound according to claim 4 wherein $R_1$ is ethyl.
6. A compound according to claim 5 wherein $R_2$ and $R_3$ are isopropyl.
7. A compound according to claim 6 wherein m is 2.
8. A compound according to claim 4 wherein
m is 2,
$R_1$ is benzyl, and
$R_2$ and $R_3$ are isopropyl.

* * * * *